United States Patent
Baca et al.

(10) Patent No.: US 8,182,814 B2
(45) Date of Patent: May 22, 2012

(54) METHODS OF TREATING INFLAMMATORY AIRWAY CONDITIONS BY INHIBITION OF IL-11 ACTIVITY

(75) Inventors: Manuel Baca, Gaithersburg, MD (US); Andrew Donald Nash, Kew (AU); Jack A. Elias, Woodbridge, CT (US)

(73) Assignees: CSL Limited, Parkville, Victoria (AU); Yale University, New Haven, CT (US)

( * ) Notice: Subject to any disclaimer, the term of this patent is extended or adjusted under 35 U.S.C. 154(b) by 0 days.

(21) Appl. No.: 12/256,883

(22) Filed: Oct. 23, 2008

(65) Prior Publication Data

US 2009/0202533 A1    Aug. 13, 2009

Related U.S. Application Data

(60) Provisional application No. 61/000,588, filed on Oct. 26, 2007.

(51) Int. Cl.
  *A61K 38/20* (2006.01)
  *C07K 14/715* (2006.01)
  *C07K 14/54* (2006.01)
  *C07K 16/28* (2006.01)
  *C07K 16/24* (2006.01)

(52) U.S. Cl. ............... 424/143.1; 424/133.1; 424/139.1; 424/141.1; 424/145.1; 530/351; 530/387.3; 530/388.22; 530/388.23

(58) Field of Classification Search .................. None
  See application file for complete search history.

(56) References Cited

U.S. PATENT DOCUMENTS

| | | | | |
|---|---|---|---|---|
| 5,679,339 | A  * | 10/1997 | Keith et al. | 424/85.2 |
| 6,540,993 | B1 * | 4/2003  | Warne et al. | 424/85.2 |
| 7,252,820 | B2 * | 8/2007  | Boodhoo et al. | 424/94.67 |
| 7,393,532 | B1 * | 7/2008  | de Sauvage et al. | 424/144.1 |
| 7,612,181 | B2 * | 11/2009 | Wu et al. | 530/387.3 |

OTHER PUBLICATIONS

Molet et al., J. Allergy Clin. Immunology 2001, 108:430-438.*
Wang, J. et al. IL-11 selectively inhibits aeroallergen-induced pulmonary eosinophilia and Th2 cytokine production. J Immunol 165, 2222-31 (2000).*
Minshall et al., J. Allergy Clin. Immunology 2000, 105:232-238.*
Kyung Sun Lee et al., "Cysteinyl leukotriene upregulates IL-11 expression in allergic airway disease of mice", *J. Allergy Clin. Immunol.*, 119(1):141-149 (Jan. 1997; published online on Oct. 27, 2006).

* cited by examiner

*Primary Examiner* — Lorraine Spector
(74) *Attorney, Agent, or Firm* — Scully, Scott, Murphy & Presser, P.C.

(57) ABSTRACT

The present invention provides a method for the treatment or prophylaxis of T-helper type 2 (Th2)-mediated disorders using antagonists of IL-11.

16 Claims, 4 Drawing Sheets

24 Hours

METHODS OF TREATING INFLAMMATORY AIRWAY CONDITIONS BY INHIBITION OF IL-11 ACTIVITY

APPLICATION DATA

This application claims priority from and the benefit of U.S. Provisional Patent Application No. 61/000,588, filed Oct. 26, 2007, the entire contents of which are incorporated herein by reference.

FIELD

The present invention provides a method for the treatment or prophylaxis of T-helper type 2 (Th2)-mediated disorders using antagonists of IL-11.

BACKGROUND

Bibliographic details of references provided in the subject specification are listed at the end of the specification.

Reference to any prior art is not, and should not be taken as, an acknowledgment of or any form of suggestion that this prior art forms part of the common general knowledge in any country.

Th2 cytokines, IL-4, IL-5, IL-9 and IL-13, are derived from T helper type 2 (Th2) cells, although they may also derive from other cell types. These Th2 cytokines play an important role in the pathophysiology of allergic diseases including asthma.

Asthma is a chronic disease that involves inflammation of the pulmonary airways and bronchial hyper-responsiveness leading to reversible obstruction of the lower airways (reviewed in Bousquet et al, *Am J Respir Crit Care Med* 161(5): 1720-1745, 2000). In a diagnostic context bronchial hyper-responsiveness is evidenced by decreased bronchial airflow following exposure to methacholine or histamine. Natural triggers that provoke airway obstruction include respiratory allergens, cold air, exercise, viral upper respiratory infection, and cigarette smoke. Bronchial provocation with allergen induces a prompt early phase immunoglobulin E (IgE)-mediated decrease in bronchial airflow followed in many patients by a late-phase IgE-mediated reaction with a decrease in bronchial airflow for 4-8 hours.

Asthmatic airways display lung hyperinflation, smooth muscle hypertrophy, fibrosis in the lamina reticularis, mucosal edema, epithelial cell sloughing, cilia cell disruption, and mucus gland hypersecretion. Microscopically, asthma is characterized by the presence of increased numbers of eosinophils, mast cells, neutrophils, lymphocytes, and plasma cells in the bronchial tissues, bronchial secretions, and mucus. Activated CD4 T-lymphocytes that produce a Th2 pattern of cytokines appear to be central to the initiation, development and maintenance of the disease phenotype (Robinson et al, *N Engl J Med* 326(5):298-304, 1992; Wills-Karp et al, *Science* 282(5397):2258-2261, 1998; Hamid et al *J Clin Invest* 87(5):1541-1546, 1991; Ray and Cohn, *J Clin Invest* 104(8):985-993, 1999). For example, the cytokines produced by these cells (including IL-4, IL-5, IL-9 and IL-13) regulate infiltration and mediator release by inflammatory cells and allergen specific antibody isotype switching from IgM to IgE. The activity of non-hemopoietic cells, for example mucus hypersecretion by goblet cells, is also regulated by Th2 cytokines.

Regardless of the triggers of asthma, the repeated cycles of inflammation in the lungs with injury to the pulmonary tissues followed by repair may produce long-term structural changes ("remodeling") of the airways.

In the most widely used animal model of human asthma, mice are sensitized to ovalbumin (ova, formulated in alum adjuvant) via the intraperitoneal route on one or more occasions. An allergic airway response is subsequently induced by single or repeated exposure to aerosol ova (generated via and ultrasonic nebulizer). Response parameters assessed over the subsequent 24-72 hr period include, for example, the accumulation of inflammatory cells and mediators in bronchoalveolar lavage (BAL) fluid, bronchorestriction following intravenous administration of methacholine (airway hyper-reactivity) and ova specific serum IgE. Histological demonstration of inflammatory cell accumulation in lung tissues and goblet cell hyperplasia/metaplasia and associated mucus hypersecretion are also key characteristics of the mouse airway response to ova. Large animal models of asthma (for example non-human primates and sheep), where lung architecture, circulation and innervation more closely resemble that of humans, have been described but are less widely used. At the time studies described in this specification were performed there were no reports of the analysis of IL-11 antagonists in either small or large animal models of asthma.

IL-11 is a pleiotropic cytokine produced by a wide variety of cell types including fibroblasts, epithelial cells, chondrocytes, endothelial cells, osteoblasts and certain tumor cells and cell lines (reviewed in Neben and Turner, *Stem Cells. Suppl* 2:156-62 1993, Du and Williams, *Blood.* 83(8):2023-2030, 1994). Human IL-11 is synthesized as a 19 kDa 199 amino acid precursor protein, with a 21 amino acid leader sequence that is removed to generate a mature secreted protein of 178 amino acids. IL-11 is highly conserved across species—the mature human and murine proteins share 88% homology at the amino acid level, while human and non-human primate IL-11 share 94% homology. Although the crystal structure of IL-11 has not been solved a variety of approaches (e.g. computer modeling and alanine scanning mutagenesis) suggest a 4 α-helical bundle structure typical of many cytokines (Czupryn et al, *Ann N Y Acad Sci* 762:152-164, 1995).

IL-11 was originally described as a soluble factor derived from stromal cells, which was capable of stimulating plasmacytoma cell proliferation (Paul et al, *Proc. Nat. Acad Sci.* 87:7512-7516, 1990). A variety of diverse biological properties have subsequently been ascribed to IL-11 including: the ability to stimulate hemopoiesis, thrombopoiesis, megakaryopoiesis (Nandurkar et al, *Blood* 90:2148, 1997; Nakashima et al, *Semin Hematol* 35(3):210-221, 1998), and bone resorption (Sims et al, *J Bone Miner Res* 20(7):1093-1102, 2005); the regulation of macrophage differentiation (Romas et al, *J Exp Med* 183(6):2581-2591, 1996); the regulation of proinflammatory cytokine synthesis including TNFα and IL-1β (Leng et al, *J Immunol* 159(5):2161-2168, 1997; Hermann et al, *Arthritis Rheum* 41(8):1388-1397, 1998; Trepicchio et al, *J Immunol* 159(11):5661-5670, 1997); the ability to confer mucosal protection after chemotherapy and radiation therapy (Orazi et al, *Lab Invest* 75(1):33-42, 1996); and as an absolute requirement for normal development of placentation and survival to birth (Robb et al, *Nat Med* 4:303, 1998). A number of these biological properties have been exploited in the development of new therapeutic strategies. Recombinant human IL-11 has been approved as a treatment for chemotherapy induced thrombocytopenia (Tepler et al, *Blood* 87(9):3607-3614, 1996) and is currently being assessed as a new approach to the treatment of chemotherapy induced gastrointestinal mucositis (Herrlinger et al, *Am J Gastroenterol* 101(4):793-797, 2006). Treatment with recombinant IL-11 in a mouse model of rheumatoid arthritis (collagen induced arthritis, CIA) caused a significant reduction in the severity of established disease, which was associated with protection from joint damage, as assessed by histology (Walmsley et al, *Immunology* 95(1):31-37, 1998). In a subsequent Phase I/II clinical study patients receiving a once weekly dose of IL-11 (15 μg/kg) demonstrated a significant reduction in the number of tender joints, although there was no overall benefit at the ACR criterion of a 20% response (Moreland et al, *Arthritis Res* 3(4):247-252, 2001). Similarly, IL-11 has shown therapeutic benefit in animal models of inflammatory bowel disease (IBD; Peterson et al, *Lab Invest* 78(12):1503-1512, 1998) and this prompted clinical studies to assess the safety and efficacy of IL-11 in patients with active Crohns disease. While IL-11 was well tolerated and provided some clinical benefit, it remained significantly inferior when compared with a standard steroid based therapy (Herrlinger et al, supra 2006).

In addition to arthritis and IBD, IL-11 has also been demonstrated to provide therapeutic benefit in mouse (Lai et al, *Nephron Exp Nephrol* 101(4):e146-154, 2005) and rat (Lai et al, *J Am Soc Nephrol* 12(11):2310-2320, 2001) models of glomerulonephritis. In these models, inflammatory disease is induced via the administration of 'nephrotoxic serum' (generated by immunization of donor animals, for example sheep, with mouse or rat glomeruli preparations) and is assessed through standard histological and urine analysis. IL-11 therapy resulted in a significant reduction in albuminuria at 24 hrs as well as a decrease in fibrinogen deposition and infiltrating inflammatory cells at 14 days post induction of disease (Lai et al, supra 2005).

In addition, IL-11 has been suggested as a potential therapeutic agent in various other inflammatory disorders including radiation-induced lung damage (Redlich et al, *J Immunol* 157(4):1iO5 10, 1996), sepsis (Chang et al, *Blood Cells Mol Dis* 22(1):57-67, 1996) and psoriasis (Trepicchio et al, *J Clin Invest* 104(11):1527-1537, 1999). U.S. Pat. No. 6,270,759 suggests that IL-11 may be therapeutically useful for a variety of inflammatory conditions including asthma and rhinitis.

The biological properties of IL-11 (IL-11 activity) are mediated through a multimeric receptor complex that incorporates IL-11, the IL-11Rα chain and gp130 (reviewed in Taga, *J Neurochem* 67(1): 1-10, 1996) and referred to as the IL-11 receptor complex. The IL-11Rα chain binds directly to IL-11 with low affinity (kDa ~10 nM), is unique to the IL-11 receptor complex and is responsible for conferring specificity. gp130 is a shared receptor component used by members of the IL-6 ligand family (IL-6, IL-11, LIF, OSM and CNTF) and is responsible for the activation of intracellular signal transduction, primarily via the JAK/STAT pathway. Recent data suggests that the IL-11 receptor complex is a high affinity (kDa ~400-800 pM), hexameric complex that incorporates two molecules of IL-11, two molecules of IL-11Rα and two molecules of gp130 (Barton et al, *J Biol Chem* 275(46): 36197-36203, 2000).

In contrast to the potential therapeutic approaches using IL-11, antagonists of IL-11 or IL-11R have been suggested as potential therapeutics for the treatment of osteoporosis (WO9959608) and in view of the role of IL-11 in the development of placentation and survival to birth (Robb et al, supra 1998) as a contraceptive agents (WO9827996 and WO03099322).

The role of IL-11 as a mediator of airway inflammation (including asthma) has primarily been investigated in mouse models, where one approach has been to assess the impact of increasing local IL-11 concentrations, Strategies used to achieve such an increase have included the local administration of recombinant IL-11 protein or local de novo synthesis via a lung specific IL-11 transgene. The results of these studies have not been definitive and, in the context of airways disease such as asthma, the potential of IL-11 either as a target or as a novel therapeutic has remained unclear.

Einarsson et al, *J Clin Invest* 97(4):915-924, 1996 demonstrated that respiratory pathogens linked to asthma exacerbation (in contrast to other viral and bacterial pathogens) were potent stimulators of lung stromal cell IL-11 production in vitro. Consistent with this observation, IL-11 was readily detectable in aspirates from children with upper respiratory tract infections but not in aspirates from uninfected children—interestingly the highest levels of IL-11 were detected in aspirates from children with clinical bronchospasm. When instilled into the lungs of mice, recombinant IL-11 induced a marked increase in sensitivity to methacholine and a mild mononuclear inflammatory response. In a subsequent report Tang et al, *J. Clin. Invest.* 98:2845, 1996 generated transgenic mice in which constitutive over-expression of IL-11 was targeted to the lung using the CC-10 promoter (CC-10/IL-11 Tg mice). In contrast to wildtype (wt) littermate controls, the transgenic animals demonstrated a nodular peribronchiolar mononuclear infiltrate with significant airways remodeling and sub-epithelial fibrosis. Furthermore, by two months of age the transgenic mice demonstrated increased airways resistance and airways hyperresponsivness to methacholine when compared with their wt littermates.

While the above studies suggest that IL-11 overexpression may contribute to the development of experimental airways inflammation, a potential role for IL-11 in the pathology of asthma is less clear. For example, cell populations known to be central to the development of asthma pathology such as eosinophils and mast cells were not detected in the infiltrates induced by IL-11. Nevertheless IL-11 mRNA and protein has been detected in the epithelial and sub-epithelial layers of human bronchial biopsies, with levels significantly greater in moderate and severe asthmatics compared to patients with mild disease and non-asthmatics (Minshall et al, *J Allergy Clin Immunol* 105(2 Pt 1):232-238, 2000).

To address this particular issue more directly Wang et al, *J. Immunol.* 165:2222, 2000 assessed the development of experimental asthma (OVA sensitization model) in the CC-10/IL-11 Tg mice. As expected OVA challenge of sensitized wt mice caused airway eosinophilic inflammation, Th2 cell accumulation, and mucus hypersecretion with mucus metaplasia. Increased levels of endothelial cell VCAM-1, mucin (Muc) 5ac gene expression and bronchoalveolar lavage and lung IL-4, IL-5, and IL-13 protein and mRNA were also noted. In contrast, OVA challenged CC10/IL-11 Tg mice that overexpressed IL-11 in the lung demonstrated lower levels of tissue and bronchoalveolar lavage inflammation, eosinophilia, and Th2 cell accumulation, and significantly lower levels of VCAM-1 and IL-4, IL-5, and IL-13 mRNA and protein. These studies demonstrate that IL-11 selectively inhibits many of the hallmarks of asthma pathology and prompted the authors to suggest that recombinant IL-11 might be used as a treatment for Th2 mediated disorders such as asthma.

More recent studies in the development of Th2 mediated disease have only served to add an additional layer of complexity (Chen et al, *J Immunol* 174(4):2305-2313, 2005). The Th2 cytokine IL-13 has been demonstrated to be key to the development of several aspects of asthma pathology including eosinophillic inflammation, mucus hypersecretion, airways hyper-responsiveness and allergen specific IgE. In agreement with these data lung-specific transgenic overexpression of IL-13 (CC-10/IL-13 Tg mice) results in the development of a severe Th2/asthma-like phenotype (Zhu et al, *J Clin Invest* 103(6):779-788, 1999). To assess a putative role for IL-11 in IL-13 activity (Chen et al, supra 2005) compared the expression of IL-11, IL-11Rα, and gp130 in lungs from wild-type mice and CC-10/IL-13 Tg mice and characterized the effects of a null mutation of IL-11Rα on the development of lung pathology in CC-10/IL-13 Tg mice. IL-13 was demonstrated to be a potent stimulator of IL-11 and IL-11Rα. Furthermore many of the pathological consequences of IL-13 overexpression, including inflammation, fibrosis, and mucus metaplasia, were substantially ameliorated in the absence of IL-11Rα. This led to the conclusion that IL-11Rα plays a key role in the pathogenesis of IL-13-induced inflammation and remodeling.

Accordingly, with respect to airway-inflammation the role of IL-11 remains unclear. In contrast, for non-airway inflammatory disease, the use of recombinant IL-11 as a novel therapeutic agent is well supported by published data.

There is a need to develop new treatments for Th2-mediated disorders such as asthma.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention relates generally to the use of antagonists of IL-11 or IL-11Rα in the treatment of Th2-mediated disorders. Th2-mediated disorders include inflammatory disorders such as asthma, chronic obstructive pulmonary disease (COPD), rhinitis, allergies and atopic dermatitis. In particular, the present invention provides the use of antagonists of IL-11 or IL-11Rα in the treatment of asthma.

The present invention is predicated in part on the elucidation of the role of IL-11 in an animal model of Th2-mediated inflammatory disorders such as asthma, and the effects of an antagonist of IL-11 or IL-11Rα in that model. In accordance with the present invention, inhibiting the activity of IL-11 is proposed to be useful in the treatment of Th2-mediated inflammatory disorders such as asthma, COPD, rhinitis, allergies and atopic dermatitis.

Accordingly, one aspect of the present invention provides a method for the treatment of a Th2-mediated disorder in a subject, the method comprising administering to the subject an amount of an antagonist of IL-11 or IL-11Rα. Reference to "an amount" includes an effective amount or an amount sufficient to ameliorate the symptoms of the Th2-mediated inflammatory disorder.

In a particular embodiment, the Th2-mediated disorder is asthma.

In another aspect the present invention provides a method for the treatment of asthma in a subject, the method comprising administering to the subject an amount of an antagonist of IL-11 or IL-11Rα.

Particular antagonists include an IL-11 mutein, an anti-IL-11 antibody, an anti-IL-11Rα antibody and a soluble IL-11Rα or functional part thereof. A "functional part" is that part of the antagonist that retains inhibitory activity towards IL-11 or IL-11Rα.

Generally, the agent is administered in an amount and for a time and under conditions sufficient to ameliorate the symptoms of the Th2-mediated inflammatory disorder.

The administration may be systemic or local. Systemic administration is particularly useful. Reference to "systemic administration" includes intra-articular, intravenous, intraperitoneal, and subcutaneous injection, infusion, as well as administration via oral, rectal and nasal routes, or via inhalation. Administration by subcutaneous injection or via inhalation is particularly useful.

The present invention further contemplates combination therapy such as targeting IL-11 and/or IL-11Rα and one or more other inflammatory targets.

Accordingly, another aspect of the present invention relates to a method for the treatment of a Th2-mediated disorder such as but not limited to asthma in a subject, the method comprising administering an antagonist of IL-11 or IL-11Rα and at least one other therapeutic agent such as an anti-inflammatory agent, a bronchodilator or an antibiotic. The co-administration may be simultaneous or sequential administration.

Particular subjects are mammals such as humans.

The present invention extends to the use of pharmaceutical compositions comprising antagonists of IL-11 or IL-11Rα. Useful compositions comprise an IL-11 mutein, an anti-IL-11 antibody, an anti-IL-11Rα antibody, or a soluble IL-11Rα.

The present invention further provides the use of an antagonist of IL-11 or IL-11Rα in the manufacture of a medicament for the treatment of a Th2-mediated disorder in a subject.

The present invention further provides the use of an antagonist of IL-11 or IL-11Rα in the manufacture of a medicament for the treatment of asthma in a subject.

A medical kit is also provided comprising an antagonist of IL-11 or IL-11Rα together with instructions to use the antagonists in the treatment of a Th2-mediated disorder such as asthma.

A summary of sequence identifiers used throughout the subject specification is provided in Table 1.

TABLE 1

Summary of sequence identifiers

| SEQUENCE ID NO: | DESCRIPTION |
|---|---|
| 1 | Murine IL-11 mutein |
| 2 | Murine IL-11 mutein |
| 3 | Murine IL-11 mutein |
| 4 | Human IL-11 mutein |
| 5 | Muc 5ac primer for rtPCR |
| 6 | Muc 5ac primer for rtPCR |

DETAILED DESCRIPTION

Figure 1:
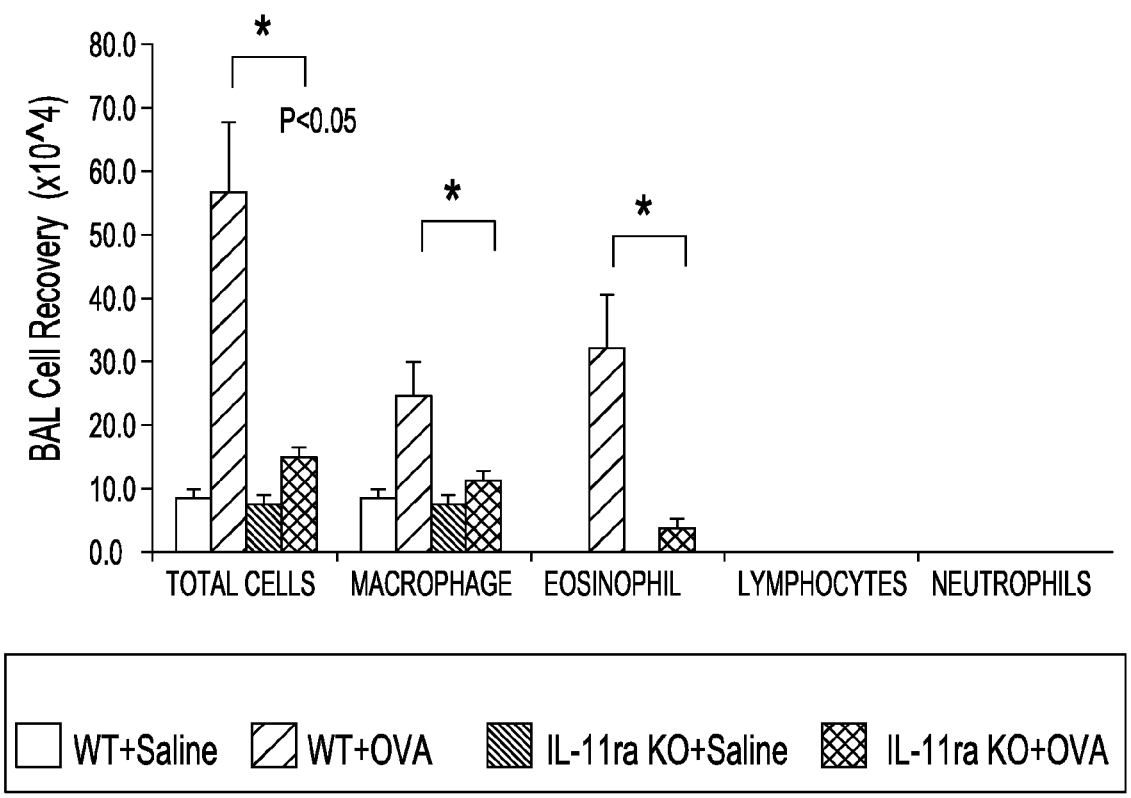
FIGS. 1, 2 and 3 are graphical representations showing the cell population in bronchoalveolar lavage (BAL) samples from wild type and IL-11Rα null mice challenged with phosphate buffered saline (PBS) control and with OVA at 24, 48 and 72 hours following exposure.

The singular forms "a", "an" and "the" include plural aspects unless the context clearly dictates otherwise. Thus, for example, reference to "a cytokine" includes a single cytokine as well as two or more cytokines; reference to "an antibody" includes a single antibody, as well as two or more antibodies; reference to "the invention" includes single and multiple aspects, of an invention; and so forth.

The present invention relates to a method for the treatment and prophylaxis of inflammatory conditions. It is predicated in part on an analysis of the use of a murine OVA-model of allergic asthma as a model of Th2-mediated inflammatory disorders.

In this model, parameters of Th2 lung inflammation, mucus metaplasia and total and antigen-specific serum IgE levels enable the determination of the effectiveness of potential therapeutic approaches in suppressing some of the key features of asthma.

Infiltration of inflammatory cells into the airways, in particular eosinophils, is an indicator of airway inflammation and a feature of asthmatic airways. The murine OVA-model of asthma results in a significant increase in the numbers of eosinophils and to a lesser extent macrophages migrating into the airways which can be easily seen in cell counts of fluid lavaged from the bronchoalveolar.

In accordance with the present invention, inhibition of IL-11 activity including signaling with a test antagonist significantly impacts on the numbers of eosinophils and macrophages migrating into the airways as determined by cell counts of fluid lavaged from the bronchoalveolar of OVA-challenged mice, indicating that the antagonism of IL-11 through inhibition of the formation of the IL-11 receptor complex is a useful therapeutic approach. These results were supported by experiments comparing IL-11Rα1 null mice with wildtype mice in the OVA-model of allergic asthma. The IL-11Rα1 null exhibited a reduction in the inflammatory response further suggesting that an antagonist of IL-11 or IL-11Rα a useful therapeutic approach.

Accordingly, the present invention provides a method for the treatment of a Th2-mediated disorder in a subject, the method comprising administering to the subject an amount of an antagonist of IL-11 or IL-11Rα.

Th2-mediated disorders include asthma, COPD, rhinitis, allergies and atopic dermatitis. A particular Th2-mediated disorder is asthma. Hence, another aspect the present invention is directed to a method for the treatment of asthma in a subject, the method comprising administering to the subject an amount of an antagonist of IL-11 or IL-11Rα.

Particular antagonists of IL-11 or IL-11Rα include an IL-11 mutein and an antibody specific for IL-11 or specific for IL-11Rα and a soluble IL-11Rα or a functional part thereof. Such a part is functional in the sense that it can still inhibit IL-11-mediated signaling.

Reference to "amount" includes an effective amount or an amount sufficient to ameliorate symptoms of the Th2-mediated disorder.

The term "an antagonist of IL-11 or IL-11Rα" as used herein means an agent that binds to IL-11 or IL-11Rα and directly inhibits the formation on cells of a multimeric receptor complex that incorporates IL-11, IL-11Rα and gp130, thus inhibiting IL-11 signaling through the IL-11 receptor complex. Such antagonists inhibit the action of IL-11 on IL-11 sensitive cells. Examples of antagonists of IL-11 or IL-11Rα are:

a. an IL-11 mutein;
b. an antibody specific for IL-11;
c. an antibody specific for IL-11R; and
d. a soluble IL-11Rα.

Antagonists of IL-11 or IL-11Rα may also include agents that specifically inhibit expression of IL-11 or IL-11R, for example antisense polynucleotides that specifically recognise a polynucleotide encoding IL-11 or the IL-11 receptor, interfering RNA that disrupt expression of IL-11 or the IL-11 receptor or ribozymes that specifically recognise a polynucleotide encoding IL-11 or the IL-11 receptor.

An antibody specific for IL-11Rα and a soluble IL-11Rα may directly bind IL-11 and thereby directly inhibit the formation on cells of a multimeric receptor complex.

Antagonists of IL-11 or IL-11Rα are known in the art, for example U.S. Pat. No. 6,998,123 describes a soluble IL-11Rα, IL-11-binding portions thereof, and commercially available antibodies to IL-11 and demonstrate their antagonist activity. Soluble forms of IL-11Rα are also described in U.S. Pat. No. 6,528,281. International Patent Publication No. WO 03/099322 describes certain IL-11 muteins and demonstrates their antagonist activity.

The term "IL-11" or its full name "interleukin-11" as used herein includes all mature forms of wild type mammalian IL-11, including murine, macaque and human, IL-11, and all truncated forms of such IL-11 that retain IL-11 signaling activity, i.e. the ability to bind with IL-11Rα and form a functional receptor complex with gp130. Mature human IL-11 is a 178 amino acid protein (i.e. lacking the 21 amino acid leader sequence of NP_000632, NCBI protein database Accession Number), and mature murine IL-11 is a 178 amino acid protein (i.e. lacking the 21 amino acid leader sequence of NP_032376, NCBI protein database Accession Number).

The term "IL-11Rα" or its full name "interleukin-11 receptor alpha" as used herein includes, but is not limited to, human IL-11Rα having the nucleotide and amino acid sequences disclosed in SEQ ID NOs:1 and 2 of International Patent Publication NO. WO 96/19574 and murine IL-11Rα having the nucleotide and amino acid sequences disclosed in SEQ ID NOs:2 and 3 of International Patent Publication No. WO 96/07737. IL-11Rα is also known as IL-11Rα1 and IL-11R and the terms may be used herein interchangeably.

The term "IL-11 mutein" as used herein refers to modified forms of mature IL-11 in which the amino acid sequence has been altered to retain effective binding to IL-11Rα but inhibit the formation of an IL-11 receptor complex with gp130. Such muteins compete with IL-11 for IL-11Rα binding and antagonize IL-11 signaling thereby inhibiting IL-11 action. Alterations to the sequence to form a mutein include amino acid substitutions of important residues for receptor binding. Conveniently, the mutein is based on human or murine IL-11 and particularly human IL-11. International Publication No. WO 03/099322 describes certain IL-11 muteins and demonstrates their antagonist activity. Muteins may be expressed in suitable host cells and purified using standard techniques. IL-111 muteins may be further modified, for example to increase their in vivo half life, including for example, by the attachment of other elements such as a PEG groups. Methods for the PEGylation of peptides are well known in the art.

The terms "antagonist", "agent", "compound", and "active" may be used interchangeably herein to refer to a substance that induces a desired pharmacological and/or physiological effect and may include the IL-11 and IL-11Rα antagonists herein described. The terms also encompass pharmaceutically acceptable and pharmacologically active forms thereof, including salts. The desired effect is the inhibition of IL-11 activity or IL-11 receptor complex signaling.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab')$_2$ fragments; and antibody-derived polypeptides produced using recombinant methods such as single chain antibodies. The terms "antibody" and "antibodies" as used herein also refer to human antibodies produced for example in transgenic animals or through phage display, as well as chimeric antibodies, humanized antibodies or primatized antibodies. The selection of fragment or modified forms of the antibodies may also involve any effect the fragments or modified forms have on their half-lives. For example, it may in certain circumstances be advantages for an antibody to have a short half-life to avoid global affects of anti-IL-11 treatment, such as neutropenia. Alternatively, where exacerbations are common or likely, an antibody with a longer half-life may be advantageous. A "half-life" for an antibody is considered herein to be short if it is within two days or less. A longer half-life for an antibody would be any half-life in excess of two days and more preferably may be greater than seven days.

The term "monoclonal antibody" is used herein to refer to an antibody obtained from a population of substantially homogeneous antibodies. That is, the individual antibodies comprising the population are identical except for naturally occurring mutations that may be present in minor amounts. The modifier "monoclonal" as used herein therefore indicates the character of the antibody as being obtained from a substantially homogeneous population of antibodies, and is not used to indicate that the antibody was produced by a particular method. For example, monoclonal antibodies in accordance with the present invention may be made by the hybridoma method described by Kohler and Milstein, *Nature* 256: 495-499, 1975, or may be made by recombinant DNA methods (such as described in U.S. Pat. No. 4,816,567). Monoclonal antibodies may also be isolated from phage antibody libraries using the techniques described in Clackson et al, *Nature* 352:624-628, 1991 or Marks et al, *J. Mol. Biol.* 222: 581-597, 1991.

Chimeric antibodies may include antibodies to IL-11 or IL-11Rα comprising the heavy and light chain variable regions of mouse, rat or rabbit antibodies to IL-11 or IL-11Rα and human heavy and light chain constant domains.

The terms "effective amount" and "therapeutically effective amount" as used herein mean a sufficient amount of an agent which provides the desired therapeutic or physiological effect or outcome, inhibiting the activity of IL-11. In addition, the effect may be an amelioration of the symptoms of the Th2-mediated disorder condition such as asthma. Undesirable effects, e.g. side effects, may sometimes manifest along with the desired therapeutic effect; hence, a practitioner balances the potential benefits against the potential risks in determining what is an appropriate "effective amount". The exact amount of agent required may vary from subject to subject depending on the species, age and general condition of the subject, mode of administration and the like. Thus, it may not be possible to specify an exact "effective amount". However, an appropriate "effective amount" in any individual case may be determined by one of ordinary skill in the art using routine experimentation. For example, the ability of an IL-11 mutein, an anti-IL-11 antibody or an anti-IL-11Rα antibody to ameliorate the effects of asthma or other Th2-mediated disorder can be evaluated in an animal model system. One of ordinary skill in the art would be able to determine the required amounts based on such factors as the subject's size, the severity of the subject's symptoms, and the particular composition or route of administration selected.

Insofar as one embodiment of the present invention relates to the use of an IL-11 mutein, an anti-IL-11 antibody or an anti-IL-11Rα antibody, the effective amount includes from about 10 μg/kg body weight to 20 mg/kg body weight of antibody such as 10, 20, 30, 40, 50, 60, 70, 80, 90, 100 μg/kg body weight, 100, 200, 300, 400, 500, 600, 700, 800, 900, 1000 μg/kg body weight or 2, 3, 4, 5, 6, 7, 8, 9, 10, 11, 12, 13, 14, 15, 16, 17, 18, 19 or 20 mg/kg body weight. Similar amounts are provided for single or combination therapy.

Reference to "Th2-mediated disorders" includes Th2-mediated inflammatory disorders such as asthma, COPD, rhinitis and allergies and atopic dermatitis. Asthma is a particular example of a Th2-mediated disorder.

A "pharmaceutically acceptable" carrier and/or diluent is a pharmaceutical vehicle comprised of a material that is not biologically or otherwise undesirable, i.e. the material may be administered to a subject along with the selected active agent without causing any or a substantial adverse reaction. Carriers may include any and all solvents, dispersion media, coatings, antibacterial and antifungal agents, agents used for adjusting tonicity, buffers, chelating agents, and absorption delaying agents and the like.

Similarly, a "pharmacologically acceptable" salt of a compound as provided herein is a salt that is not biologically or otherwise undesirable.

The terms "treating" and "treatment" as used herein refer to therapeutic treatment. For example, treatment may result in a reduction in severity and/or the frequency of symptoms of the Th2-mediated disorder, the elimination of symptoms and/or underlying cause of the inflammation, the prevention of the occurrence of symptoms of inflammation and/or their underlying cause and improvement or remediation or amelioration of damage following inflammation. Hence, the treatment may not result in a "cure" but rather an amelioration of symptoms. In addition, treatment may not commence until an exacerbated event occurs. In this context the term "prophylaxis" also applies to the prevention or treatment of a likelihood of an exacerbated event occurring.

The terms "treating" and "treatment" as used herein also refer to the reduction of one or more symptoms or characteristics associated with Th2-mediated disorders such as asthma.

The terms "condition" and "disease" are used interchangeably throughout the subject specification.

A "subject" as used herein refers to an animal, particularly a mammal and more particularly a human who can benefit from the pharmaceutical compositions and methods of the present invention. Other useful mammals are laboratory test animals, examples of which include mice, rats, rabbits, guinea pigs, hamsters, cats and dogs. There is no limitation on the type of animal that could benefit from the presently described pharmaceutical compositions and methods. A subject regardless of whether a human or non-human animal may be referred to as an individual, patient, animal or recipient as well as subject. The methods of the present invention have applications in human medicine and veterinary medicine.

In one aspect the present invention provides a method for the treatment of a Th2-mediated disorder in a subject, the method comprising administering to the subject an amount of an IL-11 mutein effective to inhibit the activity of IL-11.

As indicated above, a Th2-mediated disorder is asthma, COPD, rhinitis, allergies and atopic dermatitis. Asthma is a particular condition.

Hence, another aspect of the present invention provides a method for the treatment of asthma in a subject, the method comprising administering to the subject an amount of an IL-11 mutein effective to inhibit the activity of IL-11.

In a particular aspect the IL-11 mutein comprises the amino acid sequences set forth in SEQ ID NO:1, SEQ ID NO:2, SEQ ID NO:3 or SEQ ID NO:4.

As indicated above, the subject may be a human or non-human animal.

Another useful antagonist for use in the present invention is an antibody specific for either IL-11 or IL-11Rα that inhibits IL-11 signaling or function; i.e. inhibits IL-11 signaling through the IL-11 receptor complex by inhibiting the formation of a multimeric receptor complex that incorporates IL-11, IL-11Rα and gp130. Such antibodies to IL-11 may be referred to as anti-IL-11 antibodies, and antibodies to IL-11Rα may be referred to as anti-IL-11Rα antibodies or anti-L-11R antibodies.

Antibodies are well established as useful therapeutic approaches to target cytokines and cytokine receptors similar to IL-11 and IL-11Rα, and general methods for their isolation, production and administration are well known.

Although both polyclonal and monoclonal antibodies can be readily produced monoclonal antibodies are particularly preferred as they can be generated in large quantities, are highly specific and are directed against a single antigenic site. Furthermore, the monoclonal antibody preparations are homogeneous, making them ideal for generating antigen-binding fragments and other engineered antibody derivatives for therapeutic applications.

Although polyclonal antibodies are also relatively easily prepared, they are not as useful as monoclonal antibodies as polyclonal antibody preparations typically include different antibodies directed against different antigenic sites and thus are not as suitable for generating antigen-binding fragments and other engineered antibody derivatives for therapeutic applications.

The hybridoma method described above is used in animals, such as mice, to produce monoclonal antibodies. However, antibodies derived from animals are generally unsuitable for administration to humans as they may cause an immune response. As described below, such antibodies may be modified to become suitable for administration to humans or the desired non-human subject.

The anti-IL-11 or anti-IL-11Rα antibodies, for example, may also be produced using recombinant methods (for example, in an *E. coli* expression system or other suitable host cell) well known in the art. In this approach, DNA encoding monoclonal antibodies, such as the murine monoclonal antibodies of the present invention, may be isolated from the hybridoma cell lines, sequenced using standard procedures and optionally manipulated using recombinant DNA technology. For example, the DNA may be fused to another DNA of interest, or altered (such as by mutagenesis or other conventional techniques) to add, delete, or substitute one or more nucleic acid residues. The DNA may be placed into vectors which are then transfected or transformed into appropriate host cells using methods well known in the art (such as described in U.S. Pat. Nos. 4,399,216; 4,912,040; 4,740,461 and 4,959,455). The DNA isolated from the hybridoma cell lines may also be modified to change the character of the antibody produced by its expression.

For example, chimeric forms of murine anti-IL-11 or anti-IL-11Rα monoclonal antibodies may be produced by replacing the nucleotides encoding selected murine heavy and light chain constant domains with nucleotides encoding human heavy and light chain constant domains, such as is described in U.S. Pat. No. 4,816,567 and by Morrison et al, *Proc. Nat. Acad. Sci.* 81:6851, 1984. The chimeric antibodies may then be produced in an appropriate cell line, such as a murine myeloma or CHO cell line, that has been transfected with modified DNA.

Thus, among the antibodies contemplated for use in the present invention are chimeric anti-IL-11 or anti-IL-11Rα antibodies that comprise the heavy and light chain variable regions of murine anti-IL-11 or anti-IL-11Rα monoclonal antibody fused to human heavy and light chain antibody constant domains. Similarly, chimeric antibodies may include antibodies to IL-11 or IL-11Rα comprising the heavy and light chain variable regions of other non-human animal (for example rat or rabbit) antibodies to IL-11 or IL-11Rα and human heavy and light chain constant domains.

The anti-IL-11 or anti-IL-11Rα antibodies for use in the present invention also include humanized antibodies. In general, humanized antibodies are human antibodies (the recipient antibody) in which the complementarity determining (CDR) region residues have been replaced by CDR region residues from a non-human species (the donor antibody), such as from a mouse, rat, rabbit or non-human primate. In some cases, certain framework region (FR) residues of the human antibody may also be replaced by corresponding non-human residues, or the humanized antibodies may comprise residues which are not found in the recipient antibody or in the donor antibody. These modifications are made to enhance antibody performance and affinity. In general, the humanized antibody will comprise substantially all of at least one, and typically two, variable regions, in which all or substantially all of the CDR regions correspond to those of a non-human antibody, and all or substantially all of the FRs are those of a human antibody sequence. The humanized antibody may also optionally comprise at least a portion of an antibody constant region (Fc), typically that of a human antibody. (Jones et al, *Nature* 321:522-525, 1986; Reichmann et al, *Nature* 332: 323-329, 1988; Presta, *Curr. Op. Struct. Biol.* 2:593-596, 1992; Liu et al, *Proc. Natl. Acad. Sci. USA* 84: 3439, 1987; Larrick et al, *Bio/Technology* 7: 934, 1989; Winter and Harris, *TIPS* 14: 139, 1993; Carter et al, *Proc. Nat. Acad. Sci.* 89:4285 1992). Similarly, to create a primatized antibody the murine CDR regions can be inserted into a primate framework using methods known in the art (see e.g. International Patent Publication Nos. WO 93/02108 and WO 99/55369).

Alternatively, a humanized antibody may be created by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al, *Mol. Immunol.* 28:489-498, 1991 and Pedersen et al, *J. Mol. Biol.* 235:959-973, 1994). Therefore, it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system. This procedure of humanization is referred to as "veneering" because only the surface of the antibody is altered, the supporting residues remain undisturbed.

Further, International Patent Publication No. WO 2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 2004/006955, top ranking human sequences are selected to provide the framework sequences for constructing a chimeric antibody that functionally replaces human CDR sequences with the nonhuman CDR counterparts using the selected subset member human frameworks, thereby providing a humanized antibody of high affinity and low immunogenicity without need for comparing framework sequences between the non-human and human antibodies.

The CDRs of a given antibody may be readily identified, for example using the system described by Kabat et al in *Sequences of Proteins of Immunological Interest*, 5th Ed., U.S. Department of Health and Human Services, PHS, NIH, NIH Publication No. 91-3242, 1991).

Other approaches to producing humanized antibodies are known to those in the art that may use frameworks that are substantially human, or composites of human frameworks.

In a preferred embodiment, the antibodies for use in the present invention are human monoclonal antibodies. Such human monoclonal antibodies directed against IL-11 or its receptor can be generated using transgenic or transchromosomic mice carrying parts of the human immune system rather than the mouse system. These transgenic and transchromosomic mice include mice referred to herein as HuMAb mice and KM mice.

Still further, alternative transgenic animal systems expressing human immunoglobulin genes are available in the art and can be used to raise antibodies. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and can be used to raise antibodies against IL-11 or IL-11Rα. For example, mice carrying both a human heavy chain transchromosome and a human light chain transchromosome, referred to as "TC mice" can be used; such mice are described in Tomizuka et al, *Proc. Natl. Acad. Sci. USA* 97:722-727, 2000.

Human monoclonal antibodies can also be prepared using phage display or other display methods for screening libraries of human immunoglobulin genes. Such display methods for isolating human antibodies are established in the art. See for example: U.S. Pat. Nos. 5,223,409; 5,403,484; and 5,571,698; U.S. Pat. Nos. 5,427,908 and 5,580,717; U.S. Pat. Nos. 5,969,108 and 6,172,197 and U.S. Pat. Nos. 5,885,793; 6,521,404; 6,544,731; 6,555,313; 6,582,915 and 6,593,081.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767.

The anti-IL-11 or anti-IL-11Rα antibodies of the present invention also include antigen-binding fragments such as Fv, Fab, Fab' and F(ab')$_2$ fragments. Traditionally, antigen-binding fragments were generated by the proteolytic digestion of full antibodies (Morimoto et al, *Journal of Biochemical and Biophysical Methods* 24:107-117, 1992; Brennan et al, *Science* 229:81, 1985). A number of recombinant methods have now been developed for producing antigen-binding fragments of antibodies directly in recombinant host cells.

For example, Fab'-SH fragments can be directly recovered from *E. coli* and chemically coupled to form F(ab')$_2$ fragments (Carter et al, *Bio/Technology* 10:163-167, 1992). F(ab')$_2$ fragments can also be formed using the leucine zipper GCN4 to promote assembly of the F(ab')$_2$ molecule. Fv, Fab or F(ab')$_2$ fragments can also be isolated directly from recombinant host cell cultures. A number of recombinant methods have been developed for the production of single chain antibodies including those described in U.S. Pat. No. 4,946,778; Bird, *Science* 242:423, 1988, Huston et al, *Proc. Natl. Acad. Sci. USA* 85:5879, 1988 and Ward et al, *Nature* 334:544, 1989. Single chain antibodies may be formed by linking heavy ($V_H$) and light ($V_L$) chain variable region (Fv region) fragments via an short peptide linker to provide a single polypeptide chain (scFvs). The scFvs may also form dimers or trimers, depending on the length of a peptide linker between the two variable regions (Kortt et al, *Protein Engineering* 10:423, 1997). Phage display is another well known recombinant method for producing the antigen-binding fragments of the present invention.

Antigen-binding fragments for use in the present invention may be screened for desired properties and assays to identify antigen-binding fragments that bind to IL-11 or IL-11Rα and which antagonize IL-11 signaling through the IL-11Rα complex are known in the art.

Mammalian cell lines available as host cells for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used as host cells are insect cell lines, such as Sf9. cells, amphibian cells, bacterial cells, plant cells and fungal cells. Standard techniques are used for the culture of the host cells and expression of the desired peptide. For example, when recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies or other peptides can be recovered from the culture medium using standard protein purification methods. Further, expression from host cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

Antibodies expressed by different cell lines or in transgenic animals may have different glycosylation patterns from each other. However, all such antibodies to IL-11 or its receptor used in the treatment of Th2-mediated disorders are part of the present invention, regardless of the glycosylation pattern of the antibodies.

Techniques are also known for deriving an antibody of a different subclass or isotype from an antibody of interest i.e., subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody.

Recombinant DNA techniques may be employed. Cloned DNA encoding particular antibody polypeptides may be employed in such procedures, e.g. DNA encoding the constant region of an antibody of the desired isotype.

Vectors available for cloning and expression in host cell lines are well known in the art, and include but are not limited to vectors for cloning and expression in mammalian cell lines, vectors for cloning and expression in bacterial cell lines, vectors for cloning and expression in phage and vectors for cloning and expression insect cell lines. The peptides can be recovered using standard protein purification methods.

In one aspect the present invention contemplates a method for the treatment of a Th2-mediated disorder in a subject said method comprising administering to said subject an amount of an anti-IL-11 antibody or anti-IL-11Rα antibody effective to inhibit IL-11 signaling.

In another aspect, the present invention contemplates a method for the treatment of asthma in a subject said method comprising administering to said subject an amount of an anti-IL-11 antibody or anti-IL-11Rα antibody effective to inhibit IL-11 signaling.

In another aspect, antibodies for use in the method of the present invention are human or humanized anti-IL-11 or anti-IL-11Rα antibodies.

Preferably, the human or humanized anti-IL-11 or anti-IL-11Rα antibodies are in isolated, homogenous or fully or partially purified form.

More preferably, the human or humanized anti-IL-11 or anti-IL-11Rα antibodies are full-length monoclonal antibodies or antigen-binding fragments.

As indicated above, the selection of antigen-binding fragments or modified forms of the antibodies may be influenced by the effect the fragments or modified forms have on the individual half-life.

Another example of a useful agent is a soluble IL-11Rα which competes with the naturally occurring membrane-associated IL-11Rα for IL-11 interaction. Those skilled in the art can readily prepare soluble forms of the receptor, see for example U.S. Pat. No. 6,528,281 and U.S. Pat. No. 6,998,123. Soluble IL-11Rα comprise the portion of the extracellular region of IL-11Rα that is required to bind IL-11, and include sequences derived from that sequence that have 95% or greater identity to that sequence when aligned, and allowing for any gaps to maximise alignment. Preferably, soluble forms of IL-11Rα will comprise the two fibronectin domains of the extracellular region of the human IL-11 receptor, also known as domains 2 and 3. Preferably, the soluble receptor will be modified to improve the affinity for IL-11 over that of naturally occurring IL-11Rα, either by addition, deletion or substitution of from 1 to 10 amino acids, or by fusion to other peptide fragments, for example Fc fragments derived from human immunoglobulins, including modified forms of such fragments known to those skilled in the art, or domains 1-3 of the extracellular region of human gp130 with a linker between the peptides to allow for appropriate folding. The latter approach will provide a high affinity soluble IL-11Rα; similar to the soluble receptors for IL-6 reported by Ancey et al., *J Biol Chem* 278(19):16968-16972, 2003. In addition, IL-11 cytokine traps are included in the term soluble IL-11Rα. Such IL-11 cytokine traps comprise a fusion peptide comprising the extracellular region of IL-11Rα that is required to bind IL-11, an Fc fragment, domains 1-3 of the extracellular region of human gp130, with appropriate linker sequences between the various components, and each of the components (i.e. segment of IL-11Rα, Fc and gp130) may contain from 1 to 10 amino acid additions, deletions or substitutions; examples of cytokine traps are found in International Patent Publication Nos. WO 95/11303, WO 99/61630 and WO 00/18932. Soluble forms of IL-11Rα may be expressed in suitable host cells and purified using standard techniques.

In one aspect, the present invention contemplates a method for the treatment of a Th2-mediated disorder in a subject said method comprising administering to said subject an amount of a soluble IL-11Rα effective to inhibit the activity of IL-11.

In another aspect, the present invention contemplates a method for the treatment of asthma in a subject said method comprising administering to said subject an amount of a soluble IL-11Rα effective to inhibit the activity of IL-11.

Preferably the soluble IL-11Rα is derived from human IL-11Rα.

The present invention contemplates combination therapy such as targeting IL-11 activity and one or more other inflammatory targets.

Accordingly, another aspect of the present invention contemplates a method for the treatment of a Th2-mediated disorder in a subject, said method comprising administering an antagonist of IL-11 or IL-11Rα and at least one other therapeutic agent such as an anti-inflammatory, a bronchodilator or an antibiotic.

In another aspect, the present invention contemplates method for the treatment of asthma in a subject, said method comprising administering an antagonist of IL-11 or IL-11Rα and at least one other therapeutic agent such as an anti-inflammatory, a bronchodilator or an antibiotic.

Preferred antagonists include an IL-11 mutein and an anti-IL-11 or anti-IL-11Rα antibody.

Antagonists of IL-11 or IL-11Rα (e.g. antibodies, proteins such as non-signaling mutant forms of IL-11 (IL-11 muteins), soluble IL-11 receptors, etc) for use in the present invention are conveniently supplied in pharmaceutical compositions.

Administration may be systemic or local. Systemic administration is particularly useful. Reference to "systemic administration" includes intra-articular, intravenous, intraperitoneal, and subcutaneous injection, infusion, as well as administration via oral, rectal and nasal routes, or via inhalation.

Compositions suitable for systemic use include sterile aqueous solutions (where water soluble), sterile powders for the extemporaneous preparation of sterile injectable solutions, and sterile powders for inhalation. It must be stable under the conditions of manufacture and storage and must be preserved against the contaminating action of microorganisms such as bacteria and fungi. The carrier can be any pharmaceutically acceptable carriers and/or diluent, for example, water, ethanol, polyol (for example, glycerol, propylene glycol and liquid polyethylene glycol, and the like), suitable mixtures thereof and vegetable oils. The proper fluidity can be maintained, for example, by the use of superfactants. Various anti-bacterial and anti-fungal agents, for example, parabens, chlorobutanol, phenol, sorbic acid, thirmerosal and the like may be included. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin.

Sterile solutions are prepared by incorporating the active in the required amount in the appropriate solvent and optionally with other active ingredients and excipients as required, followed by filtered sterilization or other appropriate means of sterilization. In the case of sterile powders, suitable methods of preparation include vacuum drying and the freeze-drying technique which yield a powder of active ingredient plus any additionally desired ingredient which can be made at an appropriate particle size.

When the active is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like.

Dosage regimens may be adjusted to provide the optimum desired response (e.g. a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the antagonist, employed in the pharmaceutical composition, at levels lower than that required in order to achieve the desired therapeutic effect and gradually increase the dosage until the desired effect is achieved. In general, a suitable dose of a composition of the invention may be that amount of the compound which is the lowest dose effective to produce a therapeutic effect.

The present invention further provides the use of an antagonist of IL-11 or IL-11Rα in the manufacture of a medicament for the treatment of a Th2-mediated disorder in a subject.

In another aspect, the present invention provides the use of an antagonist of IL-11 or IL-11Rα in the manufacture of a medicament for the treatment of asthma in a subject.

Preferred antagonists include an IL-11 mutein and an anti-IL-11 or anti-IL-11Rα antibody.

In another aspect, the present invention is directed to the use of an IL-11 mutein or an antibody specific for IL-11 or specific for IL-11Rα in the manufacture of a medicament for the treatment of asthma in a subject.

The methods of the present invention may optionally include a step of selecting subjects with a Th2-mediated disorder, for example asthma, for treatment with an antagonist of IL-11 or IL-11Rα.

Animal models useful for testing of antagonists of IL-11 or IL-11 receptor include the murine OVA-model of allergic asthma.

In this model, parameters of Th2 lung inflammation, mucus metaplasia, and total and antigen-specific serum IgE levels enable the determination of the effectiveness of anti-IL-11/anti-IL-11Rα antibodies or other antagonists in suppressing some of the key features of asthma.

Infiltration of inflammatory cells into the airways, in particular eosinophils, is an indicator of airway inflammation and a feature of asthmatic airways. The OVA-model of asthma results in a significant increase in the numbers of eosinophils and to a lesser extent macrophages migrating into the airways which can be easily seen in cell counts of fluid lavaged from the bronchoalveolar.

In accordance with the present invention, inhibition of IL-11 activity with a test antagonist had a significant impact on the numbers of eosinophils and macrophages migrating into the airways as determined by cell counts of fluid lavaged from the bronchi and alveoli of OVA-challenged mice, indicating that the antagonism of IL-11 activity through inhibition of the formation of the IL-11 receptor complex is a useful therapeutic approach.

The present invention is further described by the following non-limiting Examples. In the Examples the following methods are employed.

EXAMPLE 1

IL-11 Mutein

A. Production of IL-11 Mutein

An IL-11 mutein of SEQ ID NO: 1 (in which the amino acid sequence AMSAG at positions 58-62 of mature murine IL-11 has been replaced with the amino acid sequence PAIDY and the tryptophan at position 147 of mature murine IL-11 has been replaced with alanine) was expressed in *E. coli* as an N-terminal His-tagged protein.

Briefly, cDNA encoding the mutein was PCR amplified and sub-cloned into a modified version of the pET15b vector (Novagen Cat #69661-3). The pET15b vector was modified by replacing the thrombin cleavage site and the multiple cloning site with AscI and EcoRI restriction sites, and to include an M13 origin of replication (enabling the vector to be used as a phagemid). The *E. coli* strain BL21-CodonPlus [Registered trade mark] (DE3)-RIL *E. coli* (Strategene cat #230245) was transformed with the pET15b-mutein construct and grown in a 400 mL shake-flask culture in superbroth containing 2% v/v glucose and 100 μg/mL ampicillin was grown to an optical density (600 nm) of 0.5. Protein expression was induced by the addition of isopropyl-β-D-thiogalactopyranoside to a final concentration of 200 uM and the culture was incubated with shaking at 37° C. for a further 4 hours. The expressed N-terminal hexahistidine-tagged mutein was purified from the *E. coli* cells (lysed in 7 M guanidinium hydrochloride) using immobilized nickel ion affinity chromatography and refolded by dialysis into PBS. Refolded samples of tagged mutein were further dialysed against 0.15% aqueous trifluoroacetic acid, and purified by reverse phase HPLC using acetonitrile gradients in 0.15% v/v trifluoroacetic acid. Samples were then lyophilized and reconstituted in a small volume of water prior to dilution with buffer.

A competition ELISA demonstrated that the binding affinity of mutein for IL-11R-Fc was approximately 20-fold higher than the binding affinity of murine W147A IL-11 for IL-11R-Fc. Murine W147A IL-11 (i.e. IL-11 in which the tryptophan at position 147 has been replaced with alanine) has been previously characterized as an antagonist of IL-11 bioactivity (Underhill-Day et al, *Endocrinology* 144; 3406-3414, 2003).

B. In Vitro Activity of Mutein

An IL-11 responsive cell line, Ba/F3 cells stably transfected with murine IL-11R/gp130, were seeded at $3 \times 10^4$ cells/well in 50 uL of Dulbecco's modified Eagle's medium containing 10% (v/v) fetal calf serum and increasing concentrations of mutein or W147A IL-11 were added in the presence of a fixed, submaximal concentration of murine IL-11 (50 pM) in a total volume of 100 uL/well. After incubation for 48 hours, proliferation was measured calorimetrically at 570 nm using 3-(4,5-dimethylthiazol-2-yl)-2,5-diphenyl tetrazolium bromide (MTT; Sigma-Aldrich). All assays were performed in duplicate and the mean values for each assay point were plotted.

Murine W147A IL-11 was able to inhibit murine IL-11 induced cell proliferation of the BaF3 cells in a dose-dependent manner. The mutein of the present example was significantly more potent at blocking murine IL-11 induced cell proliferation of the BaF3 cells, being 20 to 30-fold more potent an antagonist of murine IL-11 than murine W147A IL-11.

C. PEGylation of Mutein

To PEGylate the mutein, a Cys residue was introduced into the sequence at position 147 by site directed mutagenesis to provide a chemically reactive side-chain which can be site-specifically modified with a maleimide-derivatized PEG reagent. Furthermore, the mature murine IL-11 protein sequence has a thrombin cleavage site that results in the removal of the first 9 N-terminal amino acids. The mutein showed identical activity with and without the first 9 N-terminal amino acids so the internal thrombin site was also optimized by site directed mutagenesis by mutating amino acids $^6$Gly and $^7$Ser to $^6$Leu and $^7$Val respectively (SEQ ID NO: 2). For production of PEGylated mutein, the amino-terminal His-tag and the first 9 N-terminal amino acids were removed by thrombin digestion.

Briefly, the mutein comprising SEQ ID NO: 2 was expressed in $E.$ $coli$ and purified and refolded as described above. Lyophilized samples of this mutein were then re-suspended in thrombin cleavage buffer (150 mM NaCl, 2.5 mM $CaCl_2$, 20 mM Tris.HCl pH 8.4) at a concentration of 0-5 mg/mL and treated with 5 units of thrombin/mg protein for 4 hours at room temperature, to produce the mutein of SEQ ID NO: 3, which was then purified by reverse phase HPLC as previously described.

Lyophilized samples were resuspended at a concentration of 5 mg/mL in 1 mM aqueous acetic acid containing 5 mM tris(2-carboxyethyl)phosphine, and mixed with 4 volumes of 12.5 mg/mL mPEG2-maleimide (Nektar Therapeutics cat #2D3YOTO1) in PBS. Reactions were incubated for 16 hours at room temperature and protein-PEG conjugates were separated from unconjugated components by cation exchange chromatography on an SP Sepharose column, using a NaCl gradient in 20 mM sodium acetate, pH 5.5 buffer. Fractions containing the PEGylated products were pooled, dialyzed against 5 mM ammonium acetate buffer, pH 5.5, and then lyophilized.

Analysis of the PEGylated mutein by SDS-PAGE showed a shift in apparent molecular weight consistent with attachment of a single 40 kDa PEG moiety. The IL-11R binding affinity of PEGylated mutein was reduced approximately 5-fold relative to the binding affinity of non-PEGylated mutein, whilst the ability of PEGylated mutein to antagonize IL-11-induced Ba/F3 cell proliferation was reduced approximately 10-fold. The PEGylated mutein was, however, more potent than murine W147A IL-11 in both the IL-11R binding ELISA and the Ba/F3 cell assays.

EXAMPLE 2

Mouse OVA-Model with IL-11R Null Mice

To investigate the role of IL-11/IL-11R in the pathogenesis of allergic asthma, IL-11Rα null mice were compared with wildtype mice in the OVA-model of allergic asthma. IL-11Rα-null mice (IL-11R-/-) were provided by Drs. L. Robb and C. Glenn Begley (Walter and Eliza Hall Institute, Victoria, Australia) [Robb et al, $Nat$ $Med$ 4:303, 1998; Nandurkar et al, $Blood$ 90:2148, 1997] and were bred for more than eight generations onto a C57BL/6 genetic background. OVA sensitization and challenge were accomplished essentially as previously described by Wang et al, $J.$ $Immunol.$ 165:2222, 2000. In brief, 6- to 8-wk-old IL-11Rα-/- mice and wild type littermate controls received i.p. injections containing 20 mg of turkey ovalbumin (OVA) (Sigma, St. Louis, Mo.) complexed to alum (Resorptar, Indergen, New York, N.Y.) or alum alone on day 0. This process was repeated on day 7. Animals received aerosol challenge with OVA (1%, w/v) in endotoxin-free PBS or endotoxin-free PBS alone on days 14, 15, and 16. This was accomplished in a closed plastic aerosol chamber in which the mouse was placed for 40 minutes. The aerosol was generated via a Omron NE-U07 ultrasonic nebulizer (Omron Healthcare, Vernon Hills, Ill.). Mice were sacrificed 24, 48, or 72 hours after aerosol exposure. Endpoints for parameters of Th2 lung inflammation, mucus metaplasia, and total and antigen-specific serum IgE were compared in wildtype and IL-11Rα1 null mice.

The Effect of IL-11Rα1 on BAL Cellularity and Eosinophilia

Figure 2:
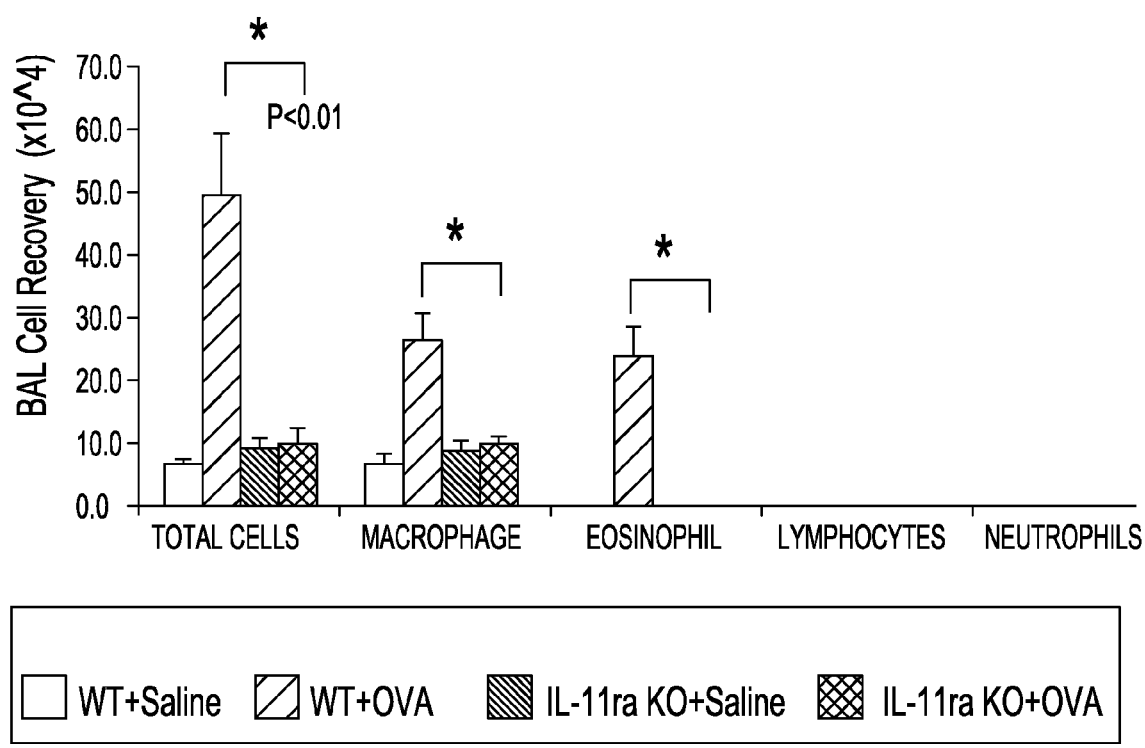
Figure 3:
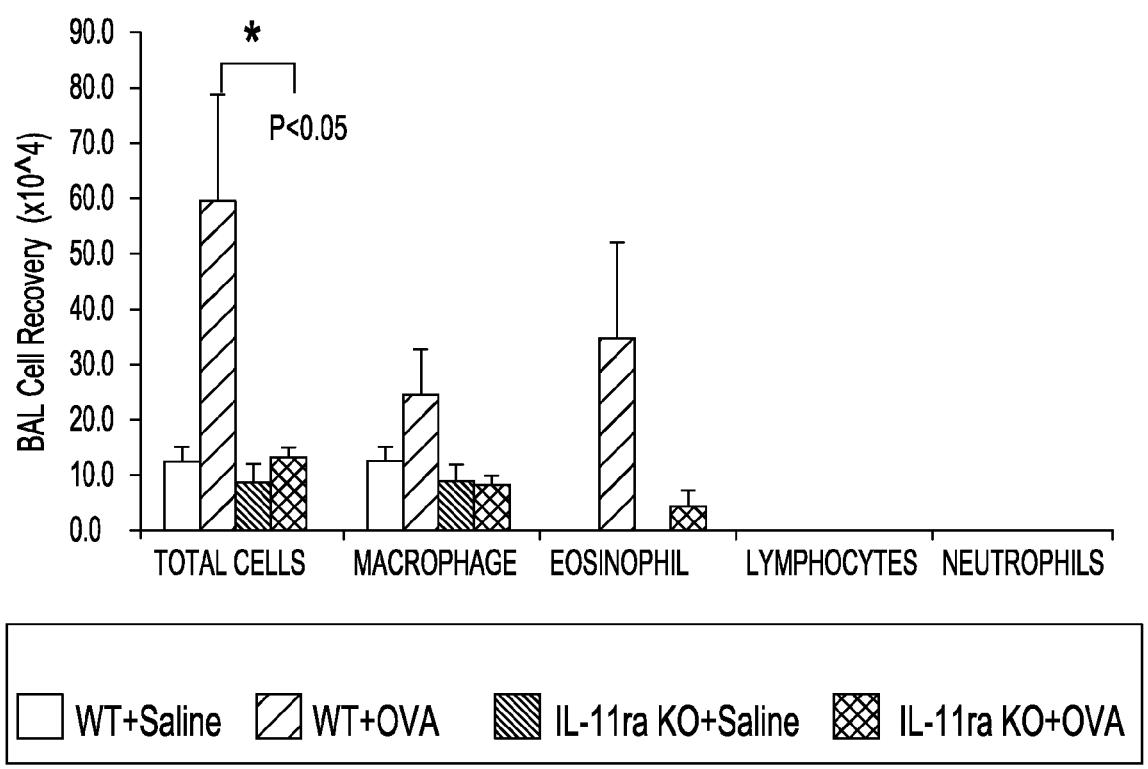

Infiltration of inflammatory cells into the airways in particular eosinophils is an indicator of airway inflammation and feature of asthmatic airways. The OVA-model of asthma results in a significant increase in the numbers of eosinophils and to a lesser extent macrophages migrating into the airways which can be easily seen in cell counts of fluid lavaged from the bronchoalveolar. Bronchoalveolar lavage (BAL) was performed as previously described (Tang et al, $J.$ $Clin.$ $Invest.$ 98:2845, 1996; Ray et al, $J.$ $Clin.$ $Invest.$ 100: 2501, 1997; Waxman et al, $J.$ $Clin.$ $Invest.$ 101:1970, 1998). In brief after anesthesia a median sternotomy was performed, the trachea was dissected free from the underlying soft tissues, and a 0.6-mm tube was inserted through a small incision in the trachea. BAL was performed by perfusing the lungs in situ with 0.6 ml of PBS and gently aspirating the fluid back. This was repeated three times. The samples were then pooled and centrifuged, and cell numbers and differentials were assessed. Total cell numbers and cell differentials are plotted in FIGS. 1, 2 and 3 for 24, 48 and 72 hrs. The significant increase in total cell numbers and specifically macrophages and eosinophils in the BAL from OVA challenged mice was essentially reversed in mice deficient in the IL-11Rα. This reduction was seen for all time points (24, 48 and 72 hrs in differential cell count) but is particularly pronounced at 48 hrs with a significance of P<0.01. This significant reduction in eosinophils and macrophils recovered from the lungs of IL-11Rα-/- mice was also be seen in 48 hr BAL cell populations stained with hematoxylin and eosin, and Diff-Quick stain.

The Effect of IL-11R on Airway Production of IL-13 mRNA and Protein.

IL-13 is a Th2 cytokine which is known to play a critical role in the pathogenesis of asthma. It is known to stimulate the production of eotaxin which is a chemo-attractant for eosinophils which contributes to eosinophilia. IL-13 also plays an important role in the production of IgE in allergic asthma where it can induce B-cells to switch antibody isotypes and increase IgE production. IL-13 protein levels in the BAL fluid and the mRNA levels in lungs of IL-11Rα1-/- and wildtype mice were compared. IL-13 in the cell-free BAL fluid generated by centrifugation of BAL samples was quantitated by ELISA using commercial kits according to the instructions provided by the manufacturers (R&D Systems, Minneapolis, Minn.). The levels of mRNA encoding IL-13 were quantitated using real time RT-PCR. Briefly, mice were sensitized and challenged, and the lungs were removed as described above. They were then digested in TRIzol reagent (Life Technologies, Grand Island, N.Y.), and total RNA was obtained by processing the tissues according to the manufacturer's specifications. The levels of specific IL-13 mRNA transcripts were then evaluated by real time RT-PCR. The cDNAs were first generated from the total RNA using High Capacity cDNA Reverse Transcription Kit (Applied Biosystems, Foster City, Calif.), then IL-13 specific PCR amplification was performed using Power SYBR Green PCR Master Mix (Applied Biosystems) and 9500 real time PCR system (Applied Biosystems). Real time PCR of b-actin was also performed for internal control. Both the levels of IL-13 mRNA and the BALF protein were significantly reduced in the IL-11Rα−/− compared with wildtype mice when challenged with OVA. The reduction in both the IL-13 protein and mRNA levels was significant (P<0.05) with the levels being comparable to those in the saline control mice.

The Effect of IL-11Rα Null Mice in Parameters of Mucus Metaplasia

Mucus hypersecretion and goblet cell hyperplasia are key characteristics of asthmatic airways and are consistently observed in models of asthma. Parameters of mucus metaplasia including mucin protein and mRNA levels in addition to histological analysis were compared in the airways of IL-11Rα−/− and wildtype mice.

Histology

Mice were anesthetized, a median sternotomy was performed, and the trachea was dissected free and cannulated as described above. The pulmonary vascular tree was then perfused with calcium- and magnesium-free PBS (pH 7.40) with a catheter in the right heart, and the lungs were inflated to 25 cm of water pressure with 11% formalin in PBS (pH 7.40). The lungs were then removed and postfixed in 10% formalin in PBS for 24 h. The tissues were processed, embedded in paraffin, sectioned, and stained with hematoxylin and eosin or diastase-periodic acid-Schiff (D-PAS). The stains were performed at the Department of Pathology of Yale University School of Medicine (New Haven, Conn.).

Slot Blotting and Immunodetection of Mucins in the BAL Fluid

To quantitate the levels of mucins in BAL fluids from IL-11Rα−/− and wildtype mice, 10, 50 and 100 μl of BAL fluid was slot blotted onto nitrocellulose membranes using a Minifold II slot blot apparatus (Schleicher & Schuell) according to the protocol provided by the manufacturer. After air-drying, the membrane was blocked with 5% skim milk in TTBS (0.1% Tween 20, 20 mM Tris-Cl, 500 mM NaCl) for 2 hours and washed three times with TTBS. The membrane was then incubated overnight at 4° C. with a monoclonal antibody against Mucin-5AC (45M1; Neo-Markers, Union City, Calif.). After washing with TTBS, the membranes were incubated for 1 hour at room temperature with horseradish peroxidase-conjugated anti-mouse or anti-goat immunoglobulin (Ig)-G(Pierce). Immunoreactive mucin was detected using a chemiluminescent procedure (ECL Plus Western blotting detection system, Amersham Biosciences) according to instructions from the manufacturer (Lee et al, *J. Biol. che.* 277:35466, 2002). A clear reduction in the level of mucin protein was seen for the OVA challenged IL-11Rα null mice compared with OVA challenged wildtype mice.

Analysis of Mucin Gene Expression

The levels of expression of mucin 5ac (Muc 5ac) was analyzed using RT-PCR analysis. Total RNA from whole lung tissue was extracted using TRIzol reagent (Life Technologies, Grand Island, N.Y.) as recommended by the manufacturer. RT-PCR was performed with the RT-PCR kit purchased from Promega (Madison, Wis.). In brief, whole lung RNA was reverse transcribed to cDNA and then amplified by PCR. The whole reaction was performed in 50 ml of reaction mixture containing 1 mM MgSO4; avian myeloblastosis virus/Tfl buffer; 0.2 mM each of dATP, dCTP, dGTP, and dTTP; 100 U/ml avian myeloblastosis virus reverse transcriptase; 100 U/ml Tfl DNA polymerase; and 1 mM each of 5' and 3' primers (48° C. for 45 min; 94° C. for 2 min; 94° C. for 45 s; annealing temperature, 1 min; 68° C. at 2 min; 68° C. at 7 min). The primers and conditions used in RT-PCR analysis were designed according to the published sequences (Spicer et al, *J. Biol. Chem.* 266:15099, 1991; Shekels et al, *Biochem. J.* 311:775, 1995). RT-PCR of β-actin was performed under the same conditions to confirm equal loading of RNA. The primers were: GTGGGCCGCTCTAGGCACCA (SEQ ID NO:5); and TGGCCTTACCCTGCAGGGGG (SEQ ID NO:6). Annealing took place at 62° C., and a 241-bp fragment was obtained (Alonzo et al, *Mol. Evol.* 23:11, 1986). The RT-PCR products and molecular weight markers were electrophoresed in 1% w/v agarose gels containing ethidium bromide and visualized by UV illumination.

Muc 5ac is one of the major mucin proteins secreted in the respiratory tract and has been shown to be up-regulated in asthma and other obstructive respiratory conditions (Ordonez et al, *Am J Respir Crit Care Med* 163(2):57-523, 2001). There is a clear and significant (P<0.05) reduction in the mRNA levels of Muc 5AC in IL-11Rα null mice compared with wildtype mice challenged with OVA consistent with the mucin protein results from the slot blot determination discussed above. Histological analysis of the airway of OVA challenged mice shows a dramatic staining of the glycoprotein-rich mucus contained in the airways of wildtype mice with diastase-periodic acid-Schiff stain. The airways of IL-11Rα null mice by comparison look similar to the saline control and lack the accumulated mucus and enlarged goblet cells.

Effect of IL-11Rα on Total and OVA-Specific IgE Antibody

IgE has been shown to have a key role in the pathogenesis of allergic asthma and total and antigen specific levels are up-regulated in the OVA-model of asthma. Serum levels of total IgE and OVA-specific IgE were measured by ELISA as previously described (Taube et al, *J. Immuno.* 169:6482, 2002; Tomkinson et al, *Am. J. Respir. Crit. Care. Med.* 163:721, 2001). Briefly, 96-well plates (Immulon 2; Dynatech, Chantilly, Va.) were coated with either OVA (5 μg/ml) or purified anti-IgE (02111D; BD PharMingen). After addition of serum samples, a biotinylated anti-IgE Ab (02122D; BD PharMingen) was used as detecting Ab, and the reaction was amplified with avidin-HRP (Sigma-Aldrich). The OVA-specific Ab titers of the samples were related to pooled standards that were generated in the laboratory and expressed as ng/ml. Total IgE levels were calculated by comparison with known mouse IgE standards (BD PharMingen). The significant increase observed in both total serum IgE and OVA-specific IgE in OVA-challenged wildtype mice was essentially reversed in IL-11Rα null mice. This reduction was statistically significant with a significance of P<0.05 and P<0.01 for the total and OVA-specific IgE respectively.

Statistical Analysis

Data were assessed for significance using Student's t test or ANOVA as appropriate.

EXAMPLE 3

The Effects of an IL-11 Antagonist in the Mouse OVA-Model

To investigate the potential of an antagonist of IL11/IL-11Rα as a therapeutic for the treatment of asthma the PEGylated IL-11 antagonist mutein of Example 1 was compared with a control PEG reagent in the mouse OVA-model of asthma.

OVA Sensitization and Challenge

OVA sensitization and challenge were accomplished essentially as previously described by Wang et al, supra 2000.

In brief 6- to 8-wk-old mice received i.p. injections containing 20 mg of turkey ovalbumin (OVA) (Sigma, St. Louis, Mo.) complexed to alum (Resorptar, Indergen, New York, N.Y.) or alum alone on day 0. This process was repeated on day 7. Animals received aerosol challenge with OVA (1%, w/v) in endotoxin-free PBS or endotoxin-free PBS alone on days 14, 15, and 16. This was accomplished in a closed plastic aerosol chamber in which the mouse was placed for 40 minutes. The aerosol was generated via a Omron NE-U07 ultrasonic nebulizer (Omron Healthcare, Vernon Hills, Ill.).

Five hundred micrograms of PEGylated mutein or control PEG reagent was administered by intraperitoneal injection daily on days 13, 14, 15, and 16. Mice were sacrificed 24 hours after the final aerosol exposure and bronchoalveolar lavage fluid from mutein and control treated mice was examined for antagonism of the asthma phenotype.

Figure 4:
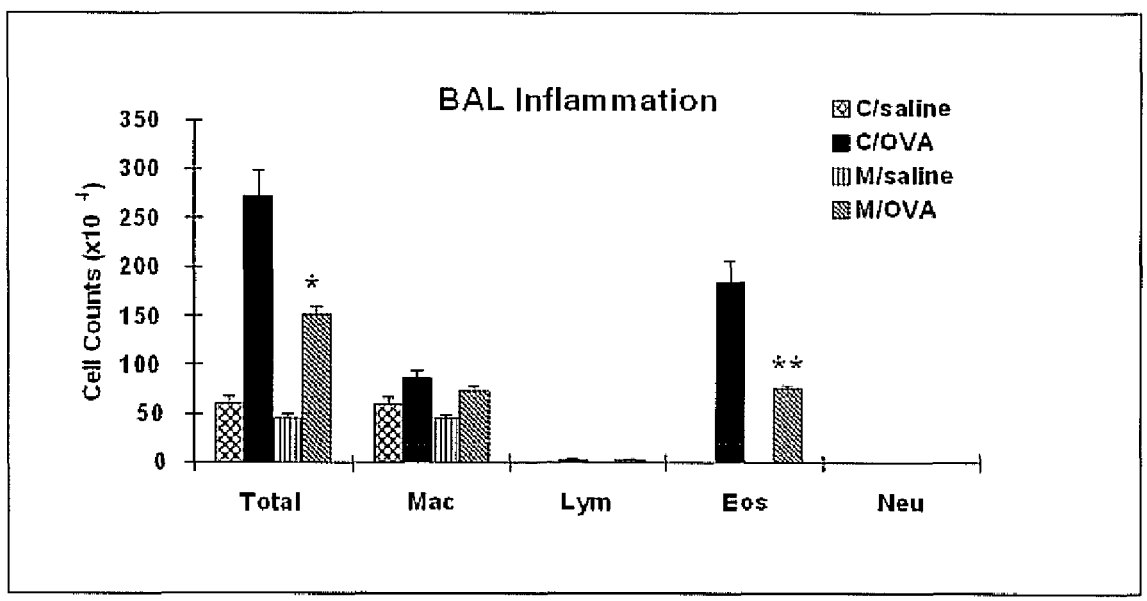
FIG. 4 is a graphical representation showing the cell population in BAL samples from wild type mice challenged with OVA and treated with either an antagonist of IL-11/IL-11Rα or with a control.

The Effect of PEGylated IL-11 Antagonist Mutein on BAL Cellularity and Eosinophilia Infiltration of inflammatory cells into the airways in particular eosinophils is an indicator of airway inflammation and feature of asthmatic airways. The OVA-model of asthma results in a significant increase in the numbers of eosinophils migrating into the airways which can be easily seen in cell counts of fluid lavaged from the bronchi and aveoli. Bronchoalveolar lavage (BAL) was performed as previously described (Tang et al, supra 1996; Ray et al, supra 1997; Waxman et al, supra 1998). In brief, after anesthesia a median sternotomy was performed, the trachea was dissected free from the underlying soft tissues, and a 0.6-mm tube was inserted through a small incision in the trachea. BAL was performed by perfusing the lungs in situ with 0.6 ml of PBS and gently aspirating the fluid back. This was repeated three times. The samples were then pooled and centrifuged, and cell numbers and differentials were assessed. Total cell numbers and cell differentials are plotted in FIG. 4 (C=wild type untreated mice and M=mutein treated mice). The significant increase in total cell numbers in the BAL from OVA challenged mice was significantly reduced in mutein treated mice compared with the PEG control ($P<0.05$). The reduction in eosinophils was highly significant ($P<0.01$) in mutein treated mice compared with the PEG control. This data demonstrates a role for an antagonist of IL-11 or IL-11R in the inhibition of the asthma phenotype in a mouse model.

The Effect of Antagonist Mutein on Parameters of Mucus Metaplasia

Mucus hypersecretion and goblet cell hyperplasia are key characteristics of asthmatic airways and are consistently observed in models of asthma.

Slot Blotting and Immunodetection of Mucins in the BAL Fluid

To quantitate the levels of mucins in BAL fluids from mutein and control treated mice 100 µl of BAL fluid was slot blotted onto nitrocellulose membranes using a Minifold II slot blot apparatus (Schleicher & Schuell) according to the protocol provided by the manufacturer. After air-drying, the membrane was blocked with 5% skim milk in TTBS (0.1% Tween 20, 20 mM Tris-Cl, 500 mM NaCl) for 2 hours and washed three times with TTBS. The membrane was then incubated overnight at 4° C. with a monoclonal antibody against Mucin-5AC (45M1; Neo-Markers, Union City, Calif.). After washing with TTBS, the membranes were incubated for 1 hour at room temperature with horseradish peroxidase-conjugated anti-mouse or anti-goat immunoglobulin (Ig)-G (Pierce). Immunoreactive mucin was detected using a chemiluminescent procedure (ECL Plus Western blotting detection system, Amersham Biosciences) according to instructions from the manufacturer and quantitated by denitometry (Lee et al, supra 2002).

Mucin 5ac is one of the major mucin proteins secreted in the respiratory tract and has been shown to be up-regulated in asthma and other obstructive respiratory conditions (Ordonez et al, supra 2001). There is a clear and significant ($P<0.05$) reduction in the levels of Muc 5AC protein in the BALF from OVA-challenged mice treated with mutein compared with control mice. This reduction is significant ($P<0.05$) with levels of mucin protein in mutein-treated mice being comparable to the saline control.

The Effect of IL-11R on Airway Production of IL-13 Protein.

IL-13 is a Th2 cytokine which is known to play a critical role in the pathogenesis of asthma. It is known to stimulate the production of eotaxin which is a chemo-attractant for eosinophils which contributes to eosinophilia. IL-13 also plays an important role in the production of IgE in allergic asthma where it can induce B-cells to switch antibody isotypes and increase IgE production. IL-13 protein levels in the BAL fluid of mice treated with mutein or the PEG control were compared. IL-13 in the cell-free BAL fluid generated by centrifugation of BAL samples was quantitated by ELISA using commercial kits according to the instructions provided by the manufacturers (R&D Systems, Minneapolis, Minn.). The levels of IL-13 protein in the BALF were significantly reduced ($P<0.05$) in the mutein treated mice compared with the PEG control mice when challenged with OVA.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Alonzo et al, *Mol Evol.* 23:11, 1986
Ancey et al., *J Biol Chem* 278(19):16968-16972, 2003
Barton et al, *J Biol Chem* 275(46):36197-36203, 2000
Bird, *Science* 242:423, 1988
Bousquet et al, *Am J Respir Crit Care Med* 161(5):1720-1745, 2000
Brennan et al, *Science,* 229:81, 1985
Carter et al, *Bio/Technology,* 10: 163-167, 1992
Carter et al, *Proc. Nat. Acad. Sci.,* 89:4285 1992
Chang et al, *Blood Cells Mol Dis* 22(1):57-67, 1996
Chen et al, *J Immunol* 174(4):2305-2313, 2005
Clackson et al, *Nature* 352:624-628, 1991
Czupryn et al, *Ann N Y Acad Sci* 762:152-164, 1995
Du and Williams, *Blood.* 83(8):2023-2030, 1994
Einarsson et al, *J Clin Invest* 97(4):915-924, 1996
Hamid et al *J Clin Invest* 87(5):1541-1546, 1991
Hermann et al, *Arthritis Rheum* 41(8):1388-1397, 1998
Herrlinger et al, *Am J Gastroenterol* 101(4):793-797, 2006
Huston et al, *Proc. Nat. Acad. Sci. USA* 85:5879, 1988
Jones et al, *Nature* 321:522-525, 1986
Kabat et al in *Sequences of Proteins of Immunological Interest,* 5th Ed., U.S. Department of Health and Human Services, PHS, NIH, NIH Publication No. 91-3242, 1991
Kohler and Milstein, *Nature* 256: 495-499, 1975
Kortt et al, *Protein Engineering* 10:423, 1997
Lai et al, *J Am Soc Nephrol* 12(11):2310-2320, 2001
Lai et al, *Nephron Exp Nephrol* 101(4):e146-154, 2005
Larrick et al, *Bio/Technology* 7: 934, 1989
Lee et al, *J. Biol. Chem.* 277:35466, 2002

Leng et al, *J Immunol* 159(5):2161-2168, 1997
Liu et al, *Proc. Natl. Acad. Sci. USA* 84: 3439, 1987
Marks et al, *J. Mol. Biol.* 222:581-597, 1991
Minshall et al, *J Allergy Clin Immunol* 105(2 Pt I):232-238, 2000
Moreland et al, *Arthritis Res* 3(4):247-252, 2001
Morimoto et al, *Journal of Biochemical and Biophysical Methods* 24:107-117, 1992
Morrison et al, *Proc. Nat. Acad. Sci.* 81:6851, 1984
Nakashima et al, *Semin Hematol* 35(3):210-221, 1998
Nandurkar et al, *Blood* 90:2148, 1997
Neben and Turner, *Stem Cells. Suppl* 2:156-62 1993
Orazi et al, *Lab Invest* 75(1):33-42, 1996
Ordonez et al, *Am J Respir Crit Care Med* 163(2):517-523, 2001
Padlan et al, *Mol. Immunol.* 28:489-498, 1991
Paul et al, *Proc. Nat. Acad Sci.* 87:7512-7516, 1990
Pedersen et al, *J. Mol. Biol.* 235:959-973, 1994
Peterson et al, *Lab Invest* 78(12):1503-1512, 1998
Presta, *Curr. Op. Struct. Biol.* 2:593-596, 1992
Ray et al, *J. Clin. Invest.* 100:2501, 1997
Ray and Cohn, *J Clin Invest* 104(8):985-993, 1999
Redlich et al, *J Immunol* 157(4):1iO5 10, 1996
Reichmann et al, *Nature* 332:323-329, 1988
Robb et al, *Nat Med* 4:303, 1998
Robinson et al, *N Engl J Med* 326(5):298-304, 1992
Romas et al, *J Exp Med* 183(6):2581-2591, 1996
Shekels et al, *Biochem. J.* 311:775, 1995
Sims et al, *J Bone Miner Res* 20(7):1093-1102, 2005
Spicer et al, *J. Biol. Chem.* 266:15099, 1991
Taga, *J Neurochem* 67(1):1-10, 1996
Tang et al, *J. Clin. Invest.* 98:2845, 1996
Taube et al, *J. Immuno.* 169:6482, 2002
Tepler et al, *Blood* 87(9):3607-3614, 1996
Tomizuka et al, *Proc. Natl. Acad. Sci. USA* 97:722-727, 2000
Tomkinson et al, *Am. J. Rspir. Crit. Care. Med.* 163:721, 2001
Trepicchio et al, *J Immunol* 159(11):5661-5670, 1997
Trepicchio et al, *J Clin Invest* 104(11):1527-1537, 1999
Walmsley et al, *Immunology* 95(1):31-37, 1998
Wang et al, *J. Immunol.* 165:2222, 2000
Ward et al, *Nature* 334:544, 1989
Waxman et al, *J. Clin. Invest.* 101:1970, 1998
Wills-Karp et al, *Science* 282(5397):2258-2261, 1998
Winter and Harris, *TIPS* 14: 139, 1993
Zhu et al, *J Clin Invest* 103(6):779-788, 1999

The invention claimed is:

1. A method for the treatment of an inflammatory airway condition in a subject, said method comprising administering to said subject an amount of an antagonist of IL-11 or IL-11Rα.

2. The method of claim 1 wherein the inflammatory airway condition is an inflammatory response in the lungs or pulmonary system.

3. The method of claim 1 wherein the inflammatory airway condition is selected from the group comprising asthma, chronic obstructive pulmonary disease (COPD), rhinitis, and allergies.

4. The method of claim 3 wherein the inflammatory airway condition is asthma.

5. The method of claim 1 wherein the antagonist is selected from the group comprising an IL-11 mutein, an antibody specific for IL-11, an antibody specific for IL-11R and a soluble IL-11Rα.

6. The method of claim 5 wherein the antagonist is an IL-11 mutein.

7. The method of claim 6 wherein the IL-11 mutein comprises an amino acid sequence selected from the group comprising SEQ ID NO:1, SEQ ID NO:2, SEQ ID NO:3 and SEQ ID NO:4.

8. The method of claim 5 wherein the antagonist is an antibody specific for IL-11- or IL-11Rα.

9. The method of claim 2 wherein the antagonist is selected from the group consisting of an IL-11 mutein, an antibody specific for IL-11, an antibody for IL-11R and a soluble IL-11Rα.

10. The method of claim 3 wherein the antagonist is selected from the group consisting of IL-11 mutein, an antibody specific for IL-11, an antibody specific for IL-11R and a soluble IL-11Rα.

11. The method of claim 4 wherein the antagonist is selected from the group consisting of an IL-11 mutein, an antibody specific for IL-11, an antibody specific for IL-11R and a soluble IL-11Rα.

12. The method of any one of claims 1-8 or 9-11 wherein the subject is a human.

13. The method of claim 12 wherein the antibody specific for IL-11 is human, humanized or chimeric.

14. The method of any one of claims 1-8 or 9-11 further comprising the administration of one of more of an anti-inflammatory agent, a bronchodilator and an antibiotic.

15. The method of claim 14 wherein the subject is a human.

16. The method of claim 15 wherein the antibody to IL-11 or IL11Rα is human, humanized or chimeric.

* * * * *

SEQUENCE LISTING

<160> NUMBER OF SEQ ID NOS: 6

<210> SEQ ID NO 1
<211> LENGTH: 178
<212> TYPE: PRT
<213> ORGANISM: Mus musculus

<400> SEQUENCE: 1

```
Pro Gly Pro Pro Ala Gly Ser Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Pro Ala Ile Asp Tyr Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Ala Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu
```

<210> SEQ ID NO 2
<211> LENGTH: 178
<212> TYPE: PRT

```
<213> ORGANISM: Mus musculus

<400> SEQUENCE: 2

Pro Gly Pro Pro Ala Leu Val Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Pro Ala Ile Asp Tyr Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Cys Gly Ser Ile Arg Ala Ala His Ala Ile Leu Gly Gly Leu
145                 150                 155                 160

His Leu Thr Leu Asp Trp Ala Val Arg Gly Leu Leu Leu Lys Thr
                165                 170                 175

Arg Leu

<210> SEQ ID NO 3
<211> LENGTH: 169
<212> TYPE: PRT
<213> ORGANISM: Mus musculus

<400> SEQUENCE: 3

Val Ser Ser Asp Pro Arg Ala Asp Leu Asp Ser Ala Val Leu Leu Thr
1               5                   10                  15

Arg Ser Leu Leu Ala Asp Thr Arg Gln Leu Ala Ala Gln Met Arg Asp
            20                  25                  30

Lys Phe Pro Ala Asp Gly Asp His Ser Leu Asp Ser Leu Pro Thr Leu
        35                  40                  45

Pro Ala Ile Asp Tyr Thr Leu Gly Ser Leu Gln Leu Pro Gly Val Leu
    50                  55                  60

Thr Arg Leu Arg Val Asp Leu Met Ser Tyr Leu Arg His Val Gln Trp
65                  70                  75                  80

Leu Arg Arg Ala Gly Gly Pro Ser Leu Lys Thr Leu Glu Pro Glu Leu
                85                  90                  95

Gly Ala Leu Gln Ala Arg Leu Glu Arg Leu Leu Arg Arg Leu Gln Leu
            100                 105                 110

Leu Met Ser Arg Leu Ala Leu Pro Gln Ala Ala Pro Asp Gln Pro Val
        115                 120                 125

Ile Pro Leu Gly Pro Pro Ala Ser Ala Cys Gly Ser Ile Arg Ala Ala
    130                 135                 140

His Ala Ile Leu Gly Gly Leu His Leu Thr Leu Asp Trp Ala Val Arg
145                 150                 155                 160

Gly Leu Leu Leu Leu Lys Thr Arg Leu
                165
```

-continued

```
<210> SEQ ID NO 4
<211> LENGTH: 169
<212> TYPE: PRT
<213> ORGANISM: Homo sapiens

<400> SEQUENCE: 4

Val Ser Pro Asp Pro Arg Ala Glu Leu Asp Ser Thr Val Leu Leu Thr
1               5                   10                  15

Arg Ser Leu Leu Ala Asp Thr Arg Gln Leu Ala Ala Gln Leu Arg Asp
            20                  25                  30

Lys Phe Pro Ala Asp Gly Asp His Asn Leu Asp Ser Leu Pro Thr Leu
        35                  40                  45

Pro Ala Ile Asp Tyr Ala Leu Gly Ala Leu Gln Leu Pro Gly Val Leu
    50                  55                  60

Thr Arg Leu Arg Ala Asp Leu Leu Ser Tyr Leu Arg His Val Gln Trp
65                  70                  75                  80

Leu Arg Arg Ala Gly Gly Ser Ser Leu Lys Thr Leu Glu Pro Glu Leu
                85                  90                  95

Gly Thr Leu Gln Ala Arg Leu Asp Arg Leu Leu Arg Arg Leu Gln Leu
            100                 105                 110

Leu Met Ser Arg Leu Ala Leu Pro Gln Pro Pro Pro Asp Pro Pro Ala
        115                 120                 125

Pro Pro Leu Ala Pro Pro Ser Ser Ala Cys Gly Gly Ile Arg Ala Ala
    130                 135                 140

His Ala Ile Leu Gly Gly Leu His Leu Thr Leu Asp Trp Ala Val Arg
145                 150                 155                 160

Gly Leu Leu Leu Leu Lys Thr Arg Leu
                165

<210> SEQ ID NO 5
<211> LENGTH: 20
<212> TYPE: PRT
<213> ORGANISM: Artificial Sequence
<220> FEATURE:
<223> OTHER INFORMATION: Muc 5ac primer

<400> SEQUENCE: 5

Gly Thr Gly Gly Gly Cys Cys Gly Cys Thr Cys Thr Ala Gly Gly Cys
1               5                   10                  15

Ala Cys Cys Ala
            20

<210> SEQ ID NO 6
<211> LENGTH: 20
<212> TYPE: PRT
<213> ORGANISM: Artificial Sequence
<220> FEATURE:
<223> OTHER INFORMATION: Muc 5ac primer

<400> SEQUENCE: 6

Thr Gly Gly Cys Cys Thr Thr Ala Cys Cys Thr Gly Cys Ala Gly
1               5                   10                  15

Gly Gly Gly Gly
            20
```